United States Patent
Meyn

[11] Patent Number: 5,026,983
[45] Date of Patent: Jun. 25, 1991

[54] METHOD AND APPARATUS FOR EXAMINING FOOD PRODUCTS BY MEANS OF IRRADIATION

[75] Inventor: Cornelis Meyn, Oostzaan, Netherlands

[73] Assignee: Meyn B.V., Oostzaan, Netherlands

[21] Appl. No.: 413,836

[22] Filed: Sep. 28, 1989

[30] Foreign Application Priority Data

Sep. 30, 1988 [NL] Netherlands ............... 8802404

[51] Int. Cl.⁵ .............................. G01N 9/04
[52] U.S. Cl. ...................... 250/223 R; 250/359.1; 250/563
[58] Field of Search ........... 250/221, 22.1, 223 R, 250/341, 353, 358.1, 359.1, 562, 563; 209/577, 581; 356/239, 387, 431

[56] References Cited
U.S. PATENT DOCUMENTS

| | | | |
|---|---|---|---|
| 4,139,307 | 2/1979 | Clarke | 356/431 |
| 4,197,457 | 4/1980 | Cheo | 250/339 |
| 4,242,583 | 12/1980 | Annis et al. | 250/358.1 |
| 4,363,966 | 12/1982 | Cheo | 250/341 |
| 4,515,165 | 5/1985 | Carroll | 250/341 |
| 4,524,276 | 6/1985 | Ohtombe | 250/341 |
| 4,590,377 | 5/1986 | Lukens | 250/358.1 |
| 4,687,442 | 7/1987 | Wagner | 250/563 |
| 4,723,659 | 2/1988 | Billion | 250/563 |
| 4,829,184 | 5/1989 | Nelson et al. | 250/341 |

Primary Examiner—David C. Nelms
Assistant Examiner—S. B. Allen
Attorney, Agent, or Firm—Dority & Manning

[57] ABSTRACT

A method for examining food products for undesired ingredients by means of laser irradiation. A laser beam scans the food products according to a predetermined pattern. Variations in the intensity of the laser beam passing through the food products indicate the presence of undesired ingredients. This method is carried out by an apparatus which comprises two parabolic mirrors, a laser emitting a laser beam so as to originate from the focus of one of the mirrors and a detection means positioned in the focus of the other mirror. The food products are moved between the mirrors by conveyor belts.

19 Claims, 1 Drawing Sheet

METHOD AND APPARATUS FOR EXAMINING FOOD PRODUCTS BY MEANS OF IRRADIATION

BACKGROUND OF THE INVENTION

The invention relates to a method for examining food products such as meat to detect undesired ingredients, such as bone fragments, by means of irradiation.

In consequence to the increased demand for a larger assortment of food products, such as meat, fish and poultry, increasing automation has occurred in the respective sectors of the industry. With such an automation, of which an example is the mechanical filleting of chickens, a higher production capacity is obtained than would be the case without automation. However, a disadvantage of such automation is that a final check of the food product is required, for example, to determine the presence of bone fragments or the like.

A known method for examining food products by means of irradiation uses X-rays. However, large scale use of X-rays for examining food products is commercially unattractive, for the consumer does not like to buy food products which have been treated with X-rays. An indication on the final product that has been examined, using X-rays, would have very negative consequences on the commercial success of such a food product.

SUMMARY OF THE INVENTION

It is an object of the invention to provide a method for examining food products by means of irradiation, which does not have this disadvantage and is not thought of in a negative way by the consumer.

The method according to the invention, is characterized in that a laser beam is used for the irradiation which scans the food product according to a predetermined pattern and, wherein, the local intensity of the laser beam passing through the food product is determined for detecting undesired ingredients.

The application of a laser beam for the irradiation of food products has absolutely no hazards for the public health. Further, a laser beam penetrates food products such as meat, fish and the like wall. The determined local intensity of the laser beam passing through the food product is substantially proportional with the density of the meat or the undesired ingredients contained therein, such that determined variations in the intensity represent a direct indication of undesired ingredients in the food product. By feeding the determined local intensity value to a computer, which takes into account the specific wave length of the laser beam, the substance of the food product as well as the substance of expected ingredients (bone, cartilage, fishbones or the like), can be determined, and undesired ingredients present in the food product can be identified.

According to a preferred embodiment of the method, according to the invention, the laser beams scans the food product on a line-by-line basis.

By means of such a line-by-line scan the computer creates an image of the local intensity variations, so that a picture is created of the undesired ingredients present.

According to another preferred embodiment of the method, according to the invention, the laser beam moves to and fro along the food product, while the food product is moved over a short distance, perpendicularly to the direction of motion of the laser beam, whenever the laser beam is in or near one of its outermost positions.

By combining of the to and fro movement of the laser beam and the stepwise advancement of the food product, the food product is scanned entirely, line-by-line.

The invention further relates to an apparatus for carrying out the method according to the invention. This apparatus comprises a laser means for moving the laser beam to and fro along the food product as well as detection means for determining the intensity of the laser beam passing through the food product.

A preferred embodiment of the apparatus, according to the invention, comprises a conveyor for the food product as well as two curved parabolic mirrors, respectively positioned above and below the conveyor. The parabolic axes of the mirrors extend in parallel to each other and substantially perpendicularly to the plane of motion of the conveyor, wherein the laser is positioned such that the laser beam is movable to and fro along the surface of one of the parabolic mirrors. However, the laser beam always originates from the focus of this parabolic mirror, and the detection means is positioned in the focus of the other parabolic mirror, wherein the conveyor near to the plane of the laser beam is transmissible for the laser beam.

This position of the parabolic mirrors and the position of the laser and the detection means make it possible for one laser beam to cover a plane which intersects the food product to be examined. In this way, it is possible to carry out a line-by-line scan of the food product.

It is advantageous if, according to a further embodiment of the invention, the laser is stationary and directed so that the laser beam hits a mirror positioned in the focus of one parabolic mirror, which is pivotable, to and fro. In this way the laser beam is moved to and fro over the surface of the one parabolic mirror while the laser itself is stationary.

If the conveyor comprises at least two conveyor belts, adjoining each other with a gap between them at the scanning plane of the laser beam, the food product can be moved through the apparatus without the conveyors presenting an obstruction for the laser beam.

BRIEF DESCRIPTION OF THE DRAWINGS

Hereafter the invention will be described by means of the drawings in which an embodiment of the apparatus according to the invention is illustrated.

DETAILED DESCRIPTION OF THE INVENTION

Figure 1:
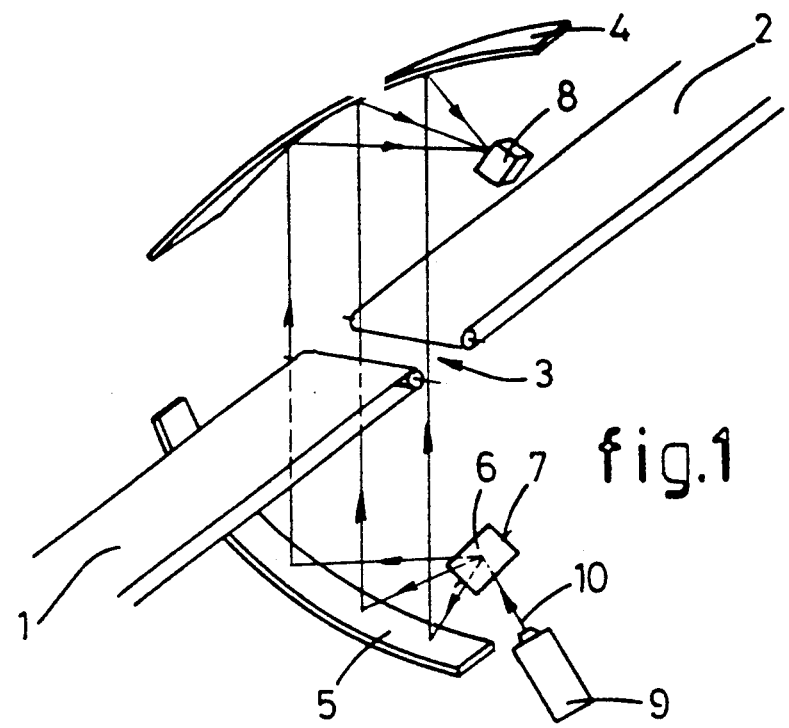
FIG. 1 is a perspective view of an embodiment of the apparatus according to the invention.

The apparatus shown in FIG. 1 comprises a conveyor means for the food product to be examined comprising two conveyor belts 1, 2. Conveyor belts 1, 2 are aligned and have a gap 3 between them.

Above and below the conveyor means oppositely curved parabolic mirrors 4 and 5 are positioned. The position of both parabolic mirrors 4, 5 is such that their parabolic axes extend mutually in parallel and substantially perpendicularly to the plane of motion of the conveyors 1, 2.

A mirror 6 is positioned in the focus of the lower parabolic mirror 5, which, in a way not shown further, is pivotable to and fro about a pivot axis 7. A detection means 8 is positioned in the focus of the upper parabolic mirror.

Moreover, FIG. 1 shows that the apparatus further comprises a laser 9 which is directed so that the emitted laser beam 10 hits the pivotable mirror 6 substantially in its pivot axis 7. The laser 9 is in a stationary position.

Figure 2:
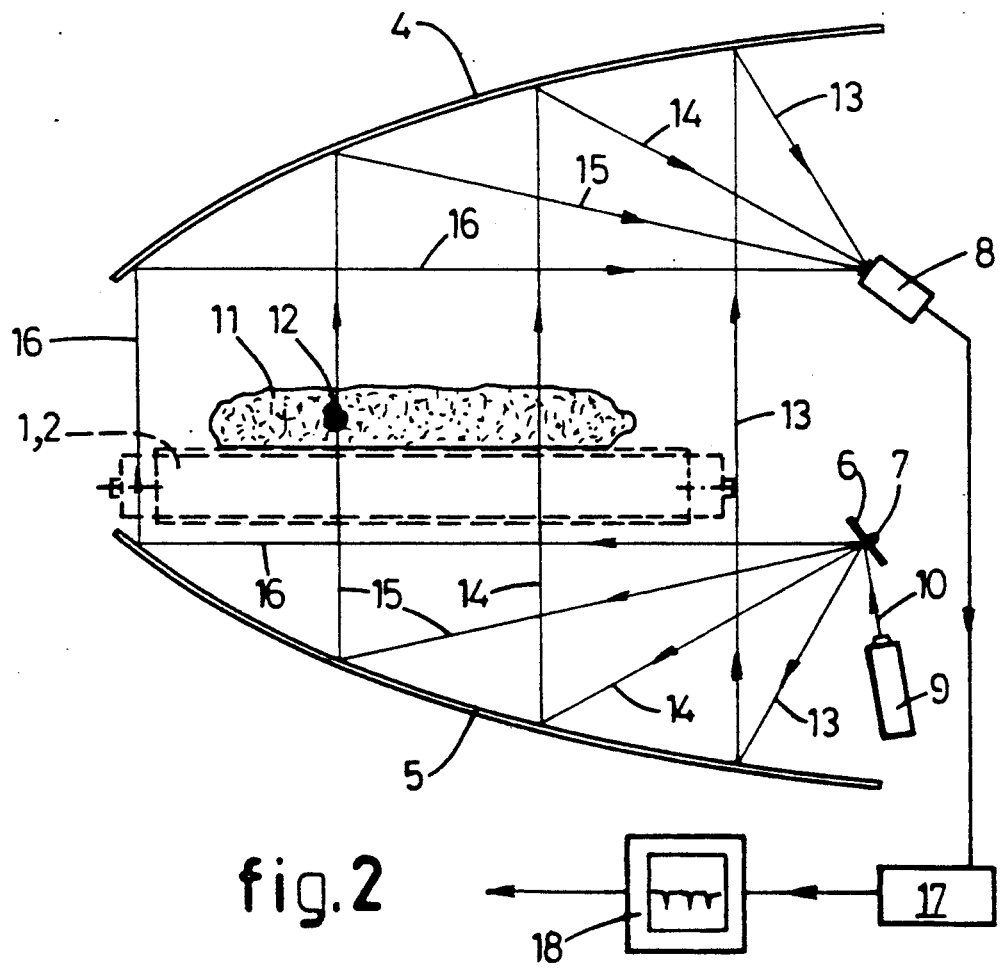
FIG. 2 illustrates the operational principle of the apparatus according to the invention.

In FIG. 2, several parts of the apparatus according to the invention are visible. Conveyors 1 and 2, upper and lower parabolic mirrors 4 and 5, respectively, mirror 6, pivotable about pivot axis 7, detection means 8, and laser 9. Laser beam 10, which originates from the laser 9, hits the mirror 6 substantially in its pivot axis 7. Moreover, in FIG. 2 a food product 11 to be examined is represented, in which an undesired ingredient, for example, a bone fragment 12, is contained.

As noted before, the laser beam 10 hits the pivotable mirror 6. Depending on the present position of the mirror 6 the reflected laser beam will hit the lower parabolic mirror 5 at different locations. In FIG. 2 this is indicated for a number of different locations by means of reflected laser beams 13-16. Since the mirror 6 is positioned in the focus of the lower parabolic mirror 5, the reflected laser beams 13-16 will, after hitting this parabolic mirror 5, be directed in parallel with each other, in the present case in a vertical plane.

Simultaneously the reflected laser beams 13-16 penetrate, depending on their position, the food product 11. In the represented position reflected laser beam 15 hits the bone fragment 12 in the food product 11.

The reflected laser beams 13-16 hit the upper parabolic mirror 4 and are focused on the detection means 8, positioned in the focus of parabolic mirror 4. In the present case this detection means 8 is a light sensitive element.

The intensity variations of the incoming laser beams (dependent on the density of the respective food product portion through which the laser beam penetrates) as determined by the detection means 8 are processed by a processing unit 17 which is connected to the detection means 8, so that an indication 18 is obtained of the presence of undesired ingredients. During this processing by means of the processing unit 17 the conveying velocity of the conveyors 1, 2 and the motion of the mirror 6 are taken into account. In this way one can determine which measured intensity belongs to what section of the food product to be examined.

Although the invention is explained above by means of an apparatus using two parabolic mirrors, it is possible to also choose a configuration which operates without parabolic mirrors. It is only essential that the laser beam is applied to scan the food product according to a predetermined pattern, and that the intensity of the laser beam passing through the food product is determined for detecting the undesired ingredients.

The invention is not limited to the embodiment described and can be varied widely within the scope of the invention.

I claim:

1. Apparatus for examining food products for the presence of undesired ingredients, such as bone fragments, which have a different density than said food products, comprising:
   (a) conveying means to convey said food products along a first path;
   (b) means for generating a laser beam;
   (c) a first parabolic mirror disposed beneath said first path, and having its parabolic axis extending in a plane which is perpendicular to said first path;
   (d) a second parabolic mirror disposed above said first path, and having its parabolic axis extending in said perpendicular plane;
   (e) means for directing and traversing said laser beam against said first parabolic mirror to reflect said laser beam in a plurality of successive parallel paths in said perpendicular plane and against said second parabolic mirror which is disposed to reflect and focus each of said reflected paths of said laser beam onto a focus point; and
   (f) detecting and measuring means disposed at said focus point for detecting and measuring intensity variations in said laser beam to detect undesired ingredients present in food products moving along said first path through said perpendicular plane.

2. Apparatus as set forth in claim 1, wherein said directing and traversing means comprises a pivoted mirror disposed within the path of said laser beam and includes means to pivot said pivoted mirror in said perpendicular plane.

3. Apparatus as set forth in claim 1, wherein said directing and traversing means comprises means for moving said laser beam.

4. Apparatus as set forth in claim 1, wherein said conveying means comprises two conveyors spaced from each other by a predetermined gap and said perpendicular plane extends through said predetermined gap.

5. Apparatus for examining food products for the presence of undesired ingredients, such as bone fragments, which have a different density than said food product, comprising:
   (a) means for conveying said food products along a first path;
   (b) means for generating a laser beam;
   (c) scanning means comprising a parabolic mirror for directing said laser beam along a plurality of spaced parallel paths in a plane perpendicular to said first path;
   (d) detecting and measuring means for detecting and measuring intensity variations in said laser beam; and
   (e) means to intercept each of said parallel paths of said laser beam and to reflect said parallel paths of said laser beam onto said detecting and measuring means to detect undesired ingredients present in said food product.

6. Apparatus for examining food products for the presence of undesired ingredients, such as bone fragments, which have a different density than said food product, comprising:
   (a) means for conveying said food products along a first path;
   (b) means for generating a laser beam;
   (c) scanning means for directing said laser beam along a plurality of spaced parallel paths in a plane perpendicular to said first path;
   (d) detecting and measuring means for detecting and measuring intensity variations in said laser beam; and
   (e) means comprising a parabolic mirror for intercepting each of said parallel paths of said laser beam and to reflect said parallel paths of said laser beam onto said detecting and measuring means to detect undesired ingredients present in said food product.

7. Apparatus for examining food products for the presence of undesired ingredients, such as bone fragments, which have a different density than said food product, comprising:
- (a) means for conveying said food products along a first path;
- (b) means for generating a laser beam;
- (c) scanning means for indexing said laser beam along a plurality of spaced parallel paths in a plane which intersects said first path;
- (d) detecting and measuring means for detecting and measuring intensity variations in said laser beam; and
- (e) means to intercept each of said parallel paths of said laser beam and to reflect said parallel paths of said laser beam onto said detecting and measuring means to detect undesired ingredients present in said food product.

8. Apparatus as set forth in claim 7, wherein said scanning means comprises a pivotable mirror disposed for pivoting motion within said perpendicular plane and disposed to intercept said laser beam and includes means to pivot said pivotable mirror in said perpendicular plane.

9. Apparatus as set forth in claim 7, wherein said means for conveying said food products along a first path comprises two conveyors spaced from one another by a gap and said perpendicular plane lies within the said gap.

10. A method for examining food products for undesired ingredients, such as bone fragments, which have a different density than said food products, comprising the following steps:
- (a) conveying said food product along a first path;
- (b) scanning said food product with a laser beam while indexing said laser beam in a plane which intersects said first path and while said beam penetrates said food product, said food product is conveyed along said first path as said food product passes through said plane; and
- (c) detecting and measuring the intensity of the laser beam passing through said food product to detect the presence of undesired ingredients therein.

11. A method as set forth in claim 10, including the step of scanning said food product with said laser beam on a line-by-line basis.

12. A method as set forth in claim 10, including the step of moving said laser beam to and fro along said food product and conveying said food product a short distance in a direction which is perpendicular to the direction of movement of said laser beam when said laser beam is adjacent one of its outermost positions.

13. A method as set forth in claim 10, including the step of maintaining the source of said laser beam stationary and reflecting said laser beam along a plurality of paths.

14. A method as set forth in claim 10, including the step of indexing said laser beam in a plane which is perpendicular to said first path.

15. A method for examining food products for undesired ingredients, such as bone fragments, which have a different density than said food products, comprising the following steps:
- (a) conveying said food product by indexing movement along said first path;
- (b) scanning said food product with a laser beam which passes through said food product as said food product is conveyed along said first path; and
- (c) detecting and measuring the intensity of the laser beam passing through said food product to detect the presence of undesired ingredients therein.

16. A method as set forth in claim 15, including the step of scanning said food product with said laser beam on a line-by-line basis.

17. A method as set forth in claim 15, including the step of moving said laser beam to and fro along said food product and conveying said food product a short distance in a direction which is perpendicular to the direction of movement of said laser beam when said laser beam is adjacent one of its outermost positions.

18. A method as set forth in claim 15, including the step of maintaining the source of said laser beam stationary and reflecting said laser beam along a plurality of paths.

19. A method as set forth in claim 15, including the step of indexing said laser beam in a plane which is perpendicular to said first path.

* * * * *